United States Patent [19]

Lavker et al.

[11] Patent Number: 5,756,094
[45] Date of Patent: May 26, 1998

[54] METHODS FOR STIMULATING FOLLICULAR GROWTH

[75] Inventors: Robert M. Lavker, Malvern, Pa.; Tung-Tien Sun, Scarsdale; Da-Wen Yu, New York, both of N.Y.

[73] Assignees: Trustees of the University of Pennsylvania, Philadelphia, Pa.; New York University Medical Center, New York, N.Y.

[21] Appl. No.: 889,545

[22] Filed: Jul. 8, 1997

Related U.S. Application Data

[63] Continuation of Ser. No. 425,786, Apr. 20, 1995, abandoned, and a continuation-in-part of Ser. No. 86,199, Jul. 1, 1993, Pat. No. 5,556,783, which is a continuation-in-part of Ser. No. 971,687, Nov. 4, 1992, Pat. No. 5,279,969, which is a continuation of Ser. No. 676,185, Mar. 27, 1991, abandoned.

[51] Int. Cl.$^6$ ............................................. A61K 37/547
[52] U.S. Cl. ........................... 424/94.64; 424/574; 514/2; 514/21
[58] Field of Search ........................ 424/94.64, 574; 514/2, 21

[56] References Cited

U.S. PATENT DOCUMENTS

| | | | |
|---|---|---|---|
| 4,596,812 | 6/1986 | Chidsey, III et al. | 514/256 |
| 5,026,691 | 6/1991 | Kligman | 514/171 |
| 5,053,403 | 10/1991 | Orentreich et al. | 514/170 |
| 5,094,857 | 3/1992 | Luderschmidt | 424/449 |
| 5,112,608 | 5/1992 | Scott et al. | 424/94.64 |
| 5,134,076 | 7/1992 | Cunningham et al. | 435/240.27 |
| 5,187,089 | 2/1993 | Scott et al. | 435/212 |
| 5,196,196 | 3/1993 | Scott et al. | 424/94.64 |
| 5,206,017 | 4/1993 | Scott | 424/94.64 |
| 5,326,562 | 7/1994 | Scott | 424/94.64 |
| 5,352,442 | 10/1994 | Proctor | 424/70 |

FOREIGN PATENT DOCUMENTS

| | | |
|---|---|---|
| WO 91/05566 | 5/1991 | WIPO. |
| 9300079 | 1/1993 | WIPO. |

OTHER PUBLICATIONS

Chomcqynski and Sacchi, "Single–Step Method of RNA Isolation by Acid Guanidinium Thoicyanate Phenol–Chloroform Extraction" *Anal. Biochem.* 1987, 162: 156–159.

Cotsarelis et al., "Existence of Slow–Cycling Limbal Epithelial Basal Cells That Can Be Preferentially Stimulated to Proliferate: Implications on Epithelial Stem Cells", in *Cell* 1989, 57: 201–209.

Cotsarelis et al., "Label–Retaining Cells Reside in the Bulge Area of Pilosecbaceous Unit: Implications for Follicular Stem Cells, Hair Cycle and Skin Carcinogenesis", *Cell* 1990, 61: 1329–1337.

Jahoda and Oliver, "The growth of vibrissa dermal papilla cells in vitro", *Br. J. Derm.* 1981, 105: 623–627.

Johoda and Oliver, "Vibrissa dermal papilla cell aggregative behaviour", *J. Embryol. exp. Morph.* 1984, 79: 211–224.

Kobayashi et al., "Segregation of keratinocyte colony–forming cells in the bulge of the rat vibrissa." *PNAS USA* 1993 90: 7391–7395.

Liang and Pardee, "Differential Display of Eukaryotic Messenger RNA by Means of the Polymerase Chain Reaction", *Science* 1992, 257: 967–971.

Rochat et al., "Location of Stem Cells of Human Hair Follicles by Clonal Analysis", *Cell* 1994, 76: 1063–1073.

Warren et al., "Improved Method for the Isolation and Cultivation of Human Scalp Dermal Papilla Cells", *J. Invest. Derm.* 1992, 98: 693–699.

Yang et al. "Upper Human Hair Follicle Contains a Subpopulation of Keratinocytes with Superior In Vitro Proliferative Potential", *J. Invest. Derm.* 1993, 101: 652–659.

*Primary Examiner*—Jean C. Witz
*Attorney, Agent, or Firm*—Law Offices of Jane Massey Licata

[57] ABSTRACT

A method of modulating hair growth by contacting selected cells with a selected growth-modulating molecule is provided. A method for hair reconstitution or transplantation by expanding selected cells in vitro and combining them with other cells that regulate hair growth are also provided. Compositions containing a growth-modulating molecule which is synthesized by follicular cells and which undergoes hair-cycle-dependent concentration changes in hair follicles are also provided.

3 Claims, No Drawings

METHODS FOR STIMULATING FOLLICULAR GROWTH

This is a continuation of application Ser. No. 08/425,786, filed Apr. 20, 1995, abandoned, and a continuation-in-part of application Ser. No. 08/086,199, filed Jul. 1, 1993, now U.S. Pat. No. 5,556,783, which is a continuation-in-part of application Ser. No. 07/971,687, filed Nov. 9, 1992, now U.S. Pat. No. 5,279,969, which is a continuation of application Ser. No. 07/676,185, filed Mar. 22, 1991, abandoned.

INTRODUCTION

This invention relates to compositions and methods for regulating hair growth. This application is a continuation-in-part of U.S. application Ser. No. 08/086,199 filed Jul. 1, 1993; which is a continuation-in-part of U.S. Ser. No. 07/971,687, filed Nov. 4, 1992, which was issued as U.S. Pat. No. 5,279,960 on Jan. 18, 1994; which was a continuation of U.S. application Ser. No. 07/676,185, filed Mar. 27, 1991, now abandoned. This invention was made in the course of research supported by the National Institutes of Health. The U.S. Government may have certain rights in this invention.

BACKGROUND OF THE INVENTION

Stem cells are by definition present in all self-renewing tissues. These cells are believed to be long-lived, have a great potential for cell division and are ultimately responsible for the homeostasis of steady-state tissues. Stem cells rarely incorporate radioisotopes after single pulse labeling indicating that they are normally slow-cycling. They can, however, be induced to enter the proliferative pool in response to certain growth stimuli. When stem cells undergo occasional cell division, they give rise to more rapidly proliferating "transient amplifying cells" ("TA") which incorporate a radiolabel such as tritiated thymidine ($^3$H-TdR) after a single exposure.

Stem cells possess many of the following properties: they are relatively undifferentiated, ultrastructurally and biochemically; they have a large proliferative potential and are responsible for the long term maintenance and regeneration of the tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell, and they are usually found in well protected, highly vascularized and innervated areas.

Positive identification of stem cells was difficult because, until the present invention, there were no known immunological or biochemical markers specific for epithelial stem cells. Since they are normally "slow-cycling", they cannot be labeled by single pulse administration of radioactive materials typically used to detect actively proliferating TA cells. It has now been found that labeling of stem cells requires continuous labeling for a prolonged period. Once labeled, these slow-cycling cells retain isotope for an extended period of time. Such cells have been termed "Label-retaining cells" or "LRCs".

Cotsarelis et al., *J. Invest. Dermol.* 1989a, 92(3) disclose a method to facilitate detection of LRCs based on the ability of slow-cycling cells to be recruited to proliferate in response to hyperplastic stimuli. Alzet™ osmotic minipumps were intraperitoneally implanted in adult SENCAR mice to deliver 20 µCi of tritiated thymidine ($^3$H-TdR) per day for 14 days. During this labeling period, 0.01% O-tetradecanoylphorbol 13-acetate (TPA) in petroleum (Pet) was applied topically once daily for 4 days to the right flank. The contralateral side was treated with Pet only. Animals were sacrificed after different periods of labeling. TPA- and Pet-treated skin was examined by light microscopy and tissue section autoradiography. It was found that TPA treatment caused marked epidermal and follicular hyperplasia, whereas Pet-treated sites did not appear morphologically altered. Fourteen days of continuous $^3$H-TdR resulted in greater than 90% labeling of all nucleated epidermal and follicular epithelial cells in both TPA- and Pet-treated sites. After 4 weeks, only a small number of cells remained labeled (LRCs). These cells were detected with greater frequency in TPA than Pet-treated epidermis. The most striking concentration of LRCs was found to occur in the follicular epithelium.

Using tritiated thymidine ($^3$H-TdR) labeling, a subpopulation of corneal epithelial basal cells located in the peripheral cornea in a region called the limbus, were identified by Cotsarelis et al., in *Cell* 1989b, 57: 201-209. These cells are normally slow-cycling but can be stimulated to proliferate in response to wounding and to administration of TPA. The corneal epithelium appears to represent an exceptional situation. LRCs were detected in the basal layer of limbal epithelium. No such cells were detected in central corneal epithelium. It was found that limbal epithelium can be selectively stimulated to proliferate by introducing a wound 1-2 mm away in the central corneal epithelium. Preferential stimulation of limbal epithelial proliferation was also observed when TPA was topically applied to the anterior surface of the eye. It was, therefore, concluded that the limbal epithelium has a greater proliferative potential than central corneal epithelium.

Label-retaining cells were identified in mouse epidermis by continually labeling with $^3$H-TdR using subcutaneous injections for seven days. This method labeled almost all epidermal cells. After chasing for four weeks, it was found that a subpopulation of epidermal basal cells maintained labeled-LRCs.

Stem cells of various epithelia share a common set of features which are summarized in FIG. 7 of Cotsarelis et al. (1989b) supra. The specific location and biological properties of corneal epithelial cells as well as the stem cells of a number of other epithelia including palmar (palm) epithelium, trunk epidermis, hair follicle, dorsal tongue epithelium, and intestinal epithelium are discussed. In FIG. 7(e) it is shown that in hair follicles, the heavily pigmented stem cells are located at the base, in close proximity with follicular papillae and associated vasculature.

In subsequent work, however, Cotsarelis et al., *Cell* 1990, 61: 1329-37, show that the hair follicle stem cells were incorrectly identified by Cotsarelis et al. (1989b) supra. In fact, label-retaining cells were found to exist exclusively in the midportion of the follicle at the arrector pili muscle attachment site termed the "bulge" area of the hair follicle (Cotsarelis 1990 supra).

The demonstration that all the slow-cycling epithelial cells of mouse vibrissa and pelage follicles are concentrated in the bulge area supports the view that follicular epithelial stem cells reside in the upper follicle in the vicinity of the bulge (Cotsarelis et al. 1990 supra; Kobayashi et al., *PNAS USA* 1993 90: 7391-5; Rochat et al., *Cell* 1994, 76: 1063-73; Yang et al. *J. Invest. Derm.* 1993, 101: 652-9).

Follicular papilla cells have been shown to play an important role in "activating" the normally slow-cycling follicular epithelial stem cells to proliferate resulting in the initiation of anagen (the growing phase of the hair cycle; Cotsarelis et al., 1990 supra). The molecular mechanism by which the follicular papilla cells actually signal the epithelial stem cells to divide is, however, obscure. A better understanding of the molecules that are synthesized and secreted by the papillary cells during specific phases of the hair cycle can greatly enhance the understanding of what controls the follicular epithelial cells to grow, to undergo apoptosis, to remain in a dormant stage for a period of time and then to resume growth. Dermal papilla specific messenger RNAs have now been identified which encode growth modulating molecules which are synthesized in large quantities by follicular cells (but not by other neighboring cells) and undergo hair-cycle-dependent changes. For example, it has now been found that nexin I is a major component of the papillae of growing, but not resting, hair follicles and is important in follicular regulation and hair growth.

SUMMARY OF THE INVENTION

Molecules which are present in follicular papilla cells, but absent in their embryologically closely related dermal fibroblasts, have now been identified using the random primer-PCR approach. After comparing approximately 20% of the total mRNA populations of rat follicular papillary cells with dermal fibroblasts cultured under identical in vitro conditions, major cDNA species that are characteristic of the papillary cells only were identified. Sequence analysis established that one of these cDNA encodes nexin I, a potent protease inhibitor that can inactivate a number of growth-regulating serine proteases including thrombin, tissue plasminogen activator and urokinase. This mRNA is present in great abundance in the papillae of both vibrissa and pelage hair follicles. Moreover, its level changes significantly during different phases of the hair cycle, peaking during anagen phase VI. Several established rat follicular papilla cell lines showed a broad range of nexin I mRNA levels which were found to correlate with each cell line's ability to support follicular epithelial cells to reconstitute follicles in athymic mice. The identification of nexin I as a major component of the papillae of growing, but not resting, hair follicles indicates that nexin I or analogues thereof can have a major role in follicular regulation and hair growth. Another dermal papilla cell cDNA has been found to encode osteopontin.

DETAILED DESCRIPTION OF THE INVENTION

The inventors located the putative stem cells of the hair follicle, and possibly the sebaceous gland and epidermis, to the bulge region of the hair follicle. Using autoradiographic techniques designed to detect slow-cycling cells (label-retaining cells; LRCs), it found, unexpectedly, that there were very few LRCs in the epidermis. Furthermore, when the hair follicle was surveyed, the inventors determined that there were no LRCs in the matrix cells comprising the bulb, which is the region that was thought to contain all of the follicle stem cells. Rather, the inventors determined that there was a subpopulation of LRCs in the upper portion of the follicle in a region known as the "bulge".

The bulge cells possess many stem cell properties. They mark the end of the permanent portion of the hair follicle. They possess a relatively primitive cytoplasm. They are normally slow-cycling, but can be stimulated to proliferate by tumor promoter, TPA. Finally, they are located in a physically well protected and well nourished area. The inventors' identification of a population of putative stem cells located exclusively in the vicinity of the bulge area is consistent with their being the long-hypothesized pluripotent stem cells, giving rise not only to the hair follicle, but also the sebaceous gland and epidermis.

The bulge is a subpopulation of outer root sheath cells located in the midportion of the follicle at the arrector pili muscle attachment site. The prior art taught that hair follicle stem cells reside in the matrix or lower bulb area of the hair bulb. The inventors' discovery provided insight into hair cycle control and the involvement of hair follicle stem cells in skin carcinogenesis and led to the development of methods for identifying and modulating the activity of slow-cycling cells for diagnostic and therapeutic purposes and for evaluating the efficacy of agents for modulating the activity of identified stem cell populations.

One of the most distinguishing features of stem cells is their slow-cycling nature. A single pulse of a radioisotope such as $^3$H-TdR will not label stem cells; labeling requires repeated administration of the isotope for a prolonged period of time. Once labeled, cells that cycle slowly retain isotopes for an extended period of time.

A discrete population of mouse hair follicle cells has been identified. These cells are slow-cycling but can be induced into the proliferative phase in response to hyperproliferative stimuli. The location of these cells was unexpected. The stem cells were not found in the matrix area of the bulb where follicular stem cells are currently thought to reside. Rather, the cells were identified in a specific area of the outer root sheath, the bulge. The bulge structure is not unique to the hair follicles of the mouse. Outer root sheath bulges are also found in human hair follicles, as well as trunk and neck skin. The bulge area has attracted so little attention by prior art workers that it is rarely even mentioned in histology text books. The realization that hair follicle stem cells may reside in the bulge area has provided new insights to the inventors into how the hair cycle is regulated and the involvement of hair follicles in skin carcinogeneses.

The Identification of Slow-Cycling Cells in Hair Follicles

Twice daily, subcutaneous injections of $^3$H-TdR were given to newborn mice over the first seven days of life resulting in the labeling of almost 100% of nuclei in mouse epidermis, hair follicles, sebaceous glands, fibroblasts, and endothelial cells. Following a four week resting period ("chase"), no LRCs were identified in the matrix area of the hair follicles indicating that the matrix does not contain slow-cycling cells. Unexpectedly, a group of LRCs was found in midfollicle, in the bulge region.

In another set of experiments, adult mice were implanted with Alzet™ osmotic minipumps continuously delivering $^3$H-TdR for two weeks. After a four week chase period, LRCs were found exclusively in the bulge region.

Upon application of TPA, normally slow-cycling cells within adult bulges were stimulated to proliferate. Once the external stimulation was removed, the bulge cells were apparently the only cells to return to their previously slow-cycling state, retaining their label for a long period of time.

The Bulge Activation Theory

The hair cycle involves three distinct phases: anagen (growing), catagen (regressing), and telogen (resting). The inventors have now discovered how this hair cycle is controlled. The bulge stem cells are activated by dermal papillae during late telogen. This is termed "bulge activation". The dermal papillae are activated by the matrix during mid-anagen. Matrix cells are in fact, TA cells; therefore, contrary to the teachings of the prior art, matrix cells have a limited proliferative potential. The upward movement of dermal papillae is important for the activation of hair stem cells. Defects in any of these elements can result in abnormal hair growth or hair loss.

A number of growth factors have been determined by the inventors to be useful for modulating stem cell activity. For example, cytokines such as Tumor Necrosis Factor (TNF), Epidermal Growth Factor (EGF), Transforming Growth Factor (TGF) and Interleukin-1 (IL-1) are believed to be useful.

Cellular targets in acute graft versus host disease have been postulated to be keratinocytes with stem cell properties. Because stem cells are normally slow cycling but proliferate rapidly upon inductive stimulation, they may be attractive targets for cytokines such as TNF. EGF has been shown to have broad biological effects. Most significantly, it has the ability to induce the proliferation of basal keratinocytes. Furthermore, it has been shown to support growth during fetal development and accelerate re-epithelialization during would healing. TGF-α has been shown to be involved in the regulation of both growth and differentiation of epithelial cells. It is known to stimulate keratinocyte growth in vitro. IL-1 is known to induce proliferative activity in epidermal cells.

In studies designed to determine the effects of cytokines on various proliferative cell populations, selected cytokines are added to explants of murine skin. Explant cultures are serially harvested at daily intervals for the first 4 days of exposure, and cytokine effects on $^3$H-TdR incorporation assessed in accordance with standard techniques.

In another series of experiments, a cohort of mice is continuously labeled for 2 weeks with $^3$H-TdR and then allowed to rest for 4 weeks. Once labeled, cells which cycle slowly retain the isotope for an extended period of time and are, thus, identified as label retaining cells. Cytokines are introduced via intradermal injection to continuously labeled/chased animals. Four hours prior to sacrifice, colcemide (4 mg/kg) is injected intraperitoneally. Animals are sacrificed at 2, 6, 12 and 24 hours after cytokine injection and skin from injected areas fixed and processed for autoradiography according to routine procedures. Appearance of labeled mitotic figures indicates that slow cycling cells have been induced to proliferate.

The Identification And Use of Growth Modulating Molecules

Messenger RNAs have now been identified which encode growth modulating molecules which are synthesized by follicular cells (but not by other neighboring cells) and which undergo hair-cycle-dependent concentration changes in the hair follicle. For example, it has now been demonstrated that nexin I message is present in large amounts in anagen follicles almost exclusively in the papillae. Nexin I message was also detected in telogen follicles; not in the papillae, but rather in keratinocytes of the lower portion of the follicle. Levels of nexin I message in several established rat follicular papillary cell lines correlated well with the cell line's ability to support follicular growth in an in vivo reconstitution assay. Another major dermal papilla-specific messenger RNA was identified which encodes osteopontin. These results establish for the first time the existence of potential growth-modulating molecules which are synthesized by follicular cells and undergo hair cycle-dependent concentration changes in the hair follicle.

Nexin I, also known as glia-derived nexin I, is a 43- to 47-kD protein. It is a potent serine-protease inhibitor. It inactivates its target proteases by forming a 1:1 covalent complex releasing in this process its own C-terminal peptide. Its target enzymes include thrombin, urokinase and tissue plasminogen activator. It has been shown to play important roles in regulating cellular growth and differentiation.

Nexin I or analogues thereof have been proposed for use in a number of different conditions. For example, U.S. Pat. No. 5,206,017 and U.S. Pat. No. 5,326,562 disclose use of pharmaceutical compositions containing nexin I in the treatment of inflammation and more specifically arthritis. U.S. Pat. No. 5,187,089 also discloses use of nexin I analogues in the treatment of inflammation; in addition, this patent discloses use of nexin I analogues in the treatment of emphysema, congenital-α-1-antitrypsin deficiency, cancer, septic shock, stroke and heart attack. U.S. Pat. Nos. 5,112,608 and 5,196,196 disclose the use of nexin I in the promotion of wound healing. U.S. Pat. No. 5,134,076 discloses the use of nexin I in neurological disorders and WO 9105566 discloses the use of nexin I as an anticoagulant.

Osteopontin message was also found in cultured follicular dermal papilla cells, but not in cultured fibroblasts. Osteopontin is known to be a major bone matrix protein; however, its presence in follicles was not previously known. Osteopontin is also a secreted protein which may be involved in the regulation of follicular epithelial growth and hair growth.

Using the random primer-PCR technique (Liang and Pardee, 1992), cDNAs of rat follicular papilla cells and skin fibroblasts that have been cultured under identical in vitro conditions were generated and compared by polyacrylamide gel electrophoresis. Fourteen 5'-upstream random primers coupled with twelve 3'-downstream NM-oligo(dT)12 primers were used to perform a total of 168 polymerase chain reactions. Each reaction gave rise to an average of about 25 cDNA bands that could be adequately resolved using a 6% polyacrylamide gel. Approximately 4200 mRNA species, an equivalence of approximately 20% of the total cellular mRNA population, were analyzed. It was found that while approximately 95% of the mRNAs of the follicular papillary cells and dermal fibroblasts were identical, each cell type possessed some unique mRNA species. A number of the cDNAs from follicular cells were cloned.

The follicular papillary and dermal fibroblastic cDNAs generated were similar except for a cDNA doublet of 210-bp and 190-bp that was present in much larger quantities in dermal papilla cells than in fibroblasts. The amplification of the upper 210-bp band frequently led to the formation of the same 210-bp/190-bp doublet, indicating that these two bands were closely related. The 210-bp CDNA was cloned and designated FP-8. Northern blot analysis confirmed that this mRNA species, about 1.3-Kb in size, was present as a major component accounting for >3% of the total mRNA in cultured follicular papillary cells. However, this mRNA species was barely detectable in cultured rat fibroblasts and human WI-38 embryonic lung fibroblasts. DNA sequencing established that this cDNA encoded nexin I, a protease inhibitor known to inactivate a number of serine proteases including thrombin, urokinase, tissue plasminogen activator and trypsin.

These data clearly established that nexin I mRNA was present in large quantities in cultured vibrissa papillary cells.

To determine whether this was also true in vivo, in situ hybridization was performed on paraffin sections of rat lip skin. The results indicated that nexin I mRNA was indeed present in abundance in vivo in the papillae of vibrissa. Cells of the "connective tissue sheath" which was contiguous to and thought to be able to generate a papilla, were devoid of nexin I message. No signal was detected in any other skin mesenchymal cells, including dermal fibroblasts, adipocytes, endothelial or muscle cells. Finally, no signal was associated with keratinocytes of the anagen phase VI hair follicle or in the epidermis.

Similar results were obtained with pelage hair follicles of rat back skin. Unlike the vibrissa follicles, which are rarely caught in the degenerative (catagen) or resting (telogen) phase, the pelage follicles traverse through the hair cycle synchronously. Large amounts of nexin I were detected in the papillae of anagen pelage follicles. The level of nexin I mRNA greatly diminished, however, in the papillae of telogen and subsequent early anagen follicles. This suggests that the nexin I message level of follicular papillae is under stringent regulation in a hair cycle-dependent manner. Although a negligible amount of nexin I message was found in the matrix keratinocytes of anagen pelage follicles, a significant number of grains were reproducibly detected over the lower follicular keratinocytes of telogen and early anagen follicles whose papillary cells were, during these phases of the hair cycle, devoid of nexin I message.

The fact that nexin I message was accumulated in the papillae of anagen follicles indicated that this molecule was involved in regulating follicular growth. A panel of immortalized rat vibrissa papillary cells was used to evaluate its role. It has been shown that these cell lines, when transplanted in combination with newborn mouse skin keratinocytes to athymic mice, exhibit a wide range of capacities to support the reconstitution of hair follicles. Messenger RNAs from cell lines known to vary greatly in their ability to support follicular formation were isolated. PCR reactions using a specific primer pair were performed to generate cDNAs including that of nexin I. The level of nexin I mRNA varied significantly among these cell lines, and correlated well with the ability of the cell line to support follicular reconstitution.

Accordingly, it has been demonstrated that nexin I message is present in large amounts in anagen follicles almost exclusively in the papillae. Nexin I message was also detected in telogen follicles; however, not in papillae, but rather in keratinocytes of the lower portion of the follicle. Levels of nexin I message in several established rat follicular papillary cell lines were demonstrated to correlate well with the ability of the cell line to support hair growth. These results established for the first time the existence of growth-modulating molecules that are present in follicular cells and which undergo hair cycle-dependent concentration changes in the hair follicle. The follicular modulating molecule, nexin I or analogues thereof, can be used to facilitate the in vitro cultivation of follicular matrix keratinocytes. Such in vitro expanded follicular epithelial cells, in combination with appropriate papillary cells, are useful for hair reconstitution, transplantation and gene therapy.

As will be obvious to those of skill in the art, other growth-modulating molecules can also be identified in accordance with the methods described in this disclosure. For the purpose of this disclosure, "growth-modulating molecules" are molecules which are synthesized by follicular cells and which undergo hair-cycle dependent concentration changes in hair follicles. For example, using these methods, the inventors have already identified a cDNA in dermal papilla cells which encodes osteopontin. Using these same methods, other growth-modulating molecules can be identified.

In the present invention, compositions are provided which comprise a growth-modulating molecule which is synthesized by follicular cells and which undergoes hair-cycle-dependent concentration changes in hair follicles, preferably nexin I or an analogue thereof. Methods for identifying such molecules have been clearly provided in this disclosure. These compositions of the present invention are useful in modulating the growth and differentiation of selected follicular cells through confluency. In this method, selected cells, such as follicular epithelial cells, are contacted with an effective amount of a selected growth-modulating molecule so that hair growth in these cells is modulated. By "effective amount" it is meant a concentration of a growth-modulating molecule which is capable of modulating hair growth. Such concentrations can be routinely determined by those of skill in the art based upon this disclosure. The compositions of the present invention are also useful for hair reconstitution or transplantation. In these methods, follicular epithelial cells are expanded in vitro by contacting the follicular epithelial cells with a selected growth-modulating molecule and combining the expanded cells with selected papillary cells. Compositions comprising a growth-modulating molecule can also be administered parenterally such as subcutaneously or intramuscularly or topically to modulate hair growth in vivo.

In general, for topical administration, a growth modulating molecule such as nexin I is not applied in pure form, but is formulated in combination with one or more excipients. The composition may include a excipient such as saline. However, "excipients" may encompass any and all solvents, dispersion media, coatings, antibacterial and antifungal agents, isotonic and absorption delaying agents and the like. The use of such agents is known in the art. Supplemental active ingredients may also be incorporated. The amount of the growth modulating molecule needed in order to modulate hair growth varies depending upon the particular individual. Further, the number of applications and the period of time over which the applications are made can vary considerably depending upon the actual state of the follicular cells. However, the precise amounts, numbers and periods of administration can be routinely determined by those of skill in the art. As a guideline, a composition comprised of 0.1 to 1.0 weight percent of a growth modulating factor such as nexin I and 99.99 to 99.0 weight percent of excipient can be applied topically on a daily basis over a period of one month.

For topical administration, it is preferred that the growth modulating molecule be formulated in a semisolid cream, ointment or gel formulation. However, the formulation may also be in the form of a solution having the growth modulating molecule therein. The type of formulation and amount of the formulation applied will be determined to a large extent by the caregiver. While a single application of the growth modulating molecule may be effective, in order to obtain the best results it may be necessary to apply it periodically, such as every day, or every other day depending upon the individual and the state of the cells being treated. Again the amount of the growth modulating molecule and the frequency at which it is applied, is a matter which can readily be determined by one skilled in the art based upon visual changes observed in hair growth.

The invention is further illustrated by the following non-limiting examples.

EXAMPLES

Example 1: Cell Culture

Vibrissa follicles were dissected individually from the lip region of young (1–2 months old) Wistar rats and their papillae squeezed out using a pair of forceps. The isolated papillae were placed in a small amount of Chang's medium (1.5 ml per 60 mm) and left undisturbed in a 37° C. incubator (5% $CO_2$) for 4 days. Under these conditions, most of the papillae formed outgrowth (Jahoda and Oliver, Br. J. Derm. 1981, 105: 623–627; Warren et al., J. Invest. Derm. 1992, 98: 693–9). Ten to twelve days later, the cells were treated with 0.1% trypsin and 0.1% EDTA in phosphate-buffered saline and the dissociated single cells were then plated in Dulbecco's Minimal Essential Medium containing 10% fetal calf serum. The lip skin tissues, from which the vibrissae have been removed, were then minced thoroughly to <1 $mm^3$ and placed under outgrowth conditions and subcultured as described above. Under these conditions, the papillary cells and dermal fibroblasts maintained distinct morphology (Jahoda and Oliver, 1981 supra; Jahoda and Oliver, J. Embro. and Exper. Morph. 1984a, 79: 211–224). The RNAs of the cultured cells were extracted in 4M guanidium chloride, purified by ultracentrifugation and treated with RNase-free bovine pancreatic DNase (Chomcqynski and Sacchi, Anal. Biochem. 1987, 162: 156–159).

Example 2: Differential Display of mRNA

Total RNAs of cultured cells were reverse-transcribed/PCRed using twelve 3"-oligo$(dT)_{12}$ primers (14-bp) coupled with fourteen 5'-random primers (10-bp oligodeoxynucleotides) according to Liang and Pardee, Science 1992, 257: 967–971. After polymerase chain reaction (PCR), the cDNAs were resolved on a 6% polyacrylamide DNA sequencing gel. The area of a dried gel containing a cDNA fragment of interest was excised and extracted by heating in distilled water at 90° C. for 5 minutes. The solubilized partial cDNA was used as the template for two rounds of reamplification using the original pair of primers. After the size of the reamplified cDNA fragment was confirmed by gel electrophoresis, the fragment was cloned into a PCRII vector and sequenced using the dideoxynucleotide procedure of Singer (US Biochemical Kit). Northern blot analysis and in situ hybridization were performed according to previously described procedures.

Example 3: In Vivo Screening of Growth-Modulating Molecules

A full-length cDNA for the growth-modulating molecule is generated by PCR using standard techniques. After cDNA cloning, a recombinant growth-modulating molecule is generated in bacteria and subsequently administered to mice to determine whether the growth-modulating molecule prolongs the anagen of the mouse hair cycle. Administration to the mouse is performed either by implanting subcutaneously heparin acrylic beads soaked in the growth-modulating molecule to be screened or by implanting a slow-releasing micro-pump which release the molecule slowly over a prolonged period. The hair cycle in mice is well characterized with newborn animals having relatively primitive follicles which develop postnatally maturing around day 19 to 21 after which they enter abruptly into a catagen and a brief telogen. The second cycle begins around day 25 lasting about 10 days before entering into a prolonged telogen of approximately 20 days. Initially, it is determined whether in vivo administration of the growth-modulating molecule prolongs the second anagen. In addition, using this model it can be determined whether the growth-modulating molecule, in comparison to control proteins such as albumin, induces the premature onset and prolongation of the third anagen, which normally occur around day 45.

What is claimed is:

1. A method of stimulating follicular growth comprising contacting follicular cells with an effective amount of a growth-modulating molecule which is synthesized by follicular cells and which undergoes hair-cycle-dependent concentration changes in hair follicles selected from the group consisting of nexin I and osteopontin.

2. The method of claim 1 wherein the growth-modulating molecule is nexin I.

3. The method of claim 1 wherein the growth-modulating molecule is osteopontin.

* * * * *

UNITED STATES PATENT AND TRADEMARK OFFICE
CERTIFICATE OF CORRECTION

PATENT NO. : 5,756,094

DATED : May 26, 1998

INVENTOR(S) :
 Lavker et al.

It is certified that error appears in the above-indentified patent and that said Letters Patent is hereby corrected as shown below:

At col 1, line 8, please delete "Nov. 9, 1992" and insert therefor --Nov. 4, 1992--..

At col 1, line 10, please delete "Mar. 22, 1991" and insert therefor --Mar. 27, 1991--. .

At col 5, line 25, please delete "would" and insert therefor --wound--.

Signed and Sealed this

Third Day of November, 1998

Attest:

Attesting Officer

BRUCE LEHMAN

Commissioner of Patents and Trademarks